United States Patent
Hsu et al.

(10) Patent No.: US 11,602,520 B2
(45) Date of Patent: Mar. 14, 2023

(54) C-MET REGULATORY COMPOSITION AND ITS METHOD FOR TREATING LIVER DISEASE

(71) Applicant: Greenyn Biotechnology Co., Ltd, Taichung (TW)

(72) Inventors: Pang-Kuei Hsu, Taichung (TW); Chun-Yi Ho, Taichung (TW); Chia-Feng Wu, Taichung (TW)

(73) Assignee: GREENYN BIOTECHNOLOGY CO., LTD, Taichung (TW)

( * ) Notice: Subject to any disclaimer, the term of this patent is extended or adjusted under 35 U.S.C. 154(b) by 0 days.

(21) Appl. No.: 17/501,620

(22) Filed: Oct. 14, 2021

(65) Prior Publication Data

US 2022/0142971 A1  May 12, 2022

Related U.S. Application Data

(60) Provisional application No. 63/092,194, filed on Oct. 15, 2020.

(51) Int. Cl.
| | |
|---|---|
| *A61K 31/36* | (2006.01) |
| *A61P 1/16* | (2006.01) |
| *A61K 45/06* | (2006.01) |
| *A61K 31/341* | (2006.01) |

(52) U.S. Cl.
CPC ............ *A61K 31/36* (2013.01); *A61K 31/341* (2013.01); *A61K 45/06* (2013.01); *A61P 1/16* (2018.01)

(58) Field of Classification Search
CPC ...... A61K 31/36; A61K 31/341; A61K 45/06; A61P 1/16
USPC ........................................................ 514/464
See application file for complete search history.

(56) References Cited

PUBLICATIONS

Chiu et al PLOS one, 2016 11(4) eo153087/1-17 (Year: 2016).*

* cited by examiner

*Primary Examiner* — Yevgeny Valenrod
(74) *Attorney, Agent, or Firm* — Muncy, Geissler, Olds & Lowe, P.C.

(57) ABSTRACT

The invention discloses a c-Met regulatory composition and its method for treating liver disease, a main component of the c-Met regulatory composition comprises Antrodin A and/or DMB (4,7-Dimethoxy-5-methyl-1,3-benzodioxole) capable of effectively regulating gene expression related to cell regeneration and cytothesis in hepatic cells, such as c-Met, Notch, etc., to achieve efficacies of repairing damaged hepatic cells and promoting hepatocyte regeneration.

6 Claims, 1 Drawing Sheet

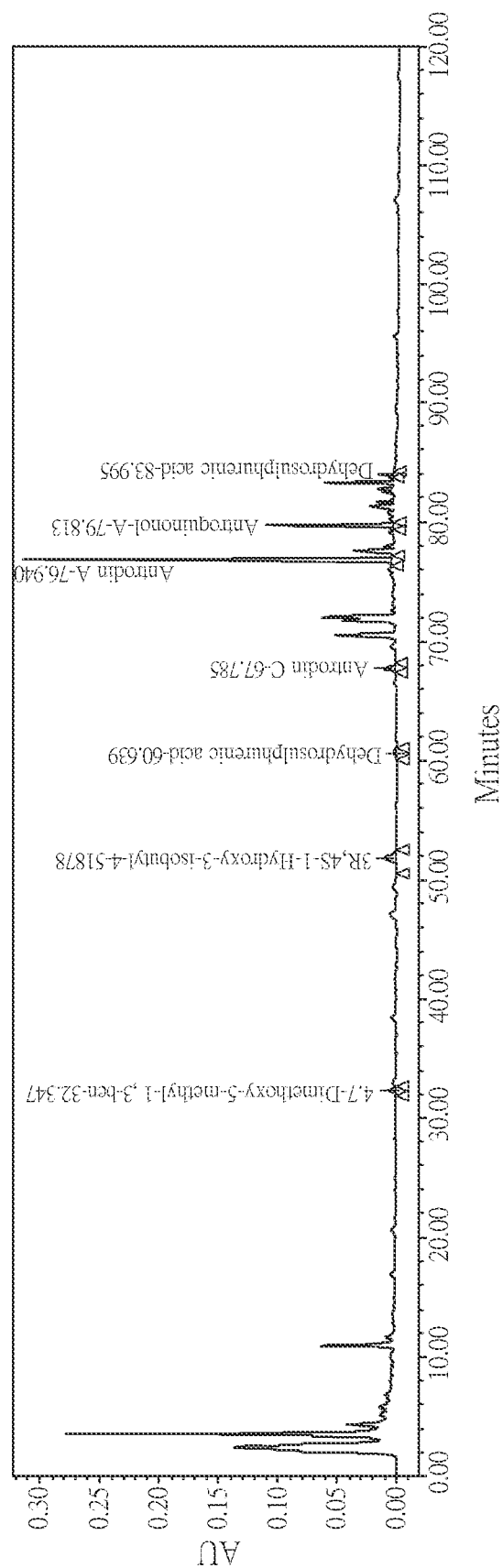

C-MET REGULATORY COMPOSITION AND ITS METHOD FOR TREATING LIVER DISEASE

CROSS REFERENCE TO RELATED APPLICATIONS

This application claims priority of U.S. Provisional Application No. 63/092,194 filed on Oct. 15, 2020 under 35 U.S.C. § 119(e), the entire contents of all of which are hereby incorporated by reference.

BACKGROUND OF THE INVENTION

Field of Invention

The invention relates to a composition related to the treatment of liver diseases, and more particularly to a c-Met regulatory composition and its method for treating liver disease.

Related Art

Liver is the center of metabolic reactions in the human body, so most chemical substances enter the liver for metabolism, making the liver very susceptible to toxic substances or their metabolites, and causing damage of liver functions, in addition to toxic substances or their metabolites, the liver can also develop hepatitis, cirrhosis or liver cancer due to viral infections.

Since the initial symptoms of liver disease are not obvious and the liver does not have pain nerves, most patients will not notice that abnormality has already occurred in the liver functions or the liver has infected with virus. Therefore, most patients with liver disease will not notice until the liver disease is more serious, which makes it more difficult to treat clinically. Take the treatment of hepatitis as an example, at present, clinically drugs are administered according to the cause of the disease or therapeutic methods corresponding to the cause are given. For example, hepatitis caused by virus will be treated with antiviral drugs: in case of hepatitis caused by fatty liver, weight control will be used to slow down the deterioration of hepatitis; but if hepatitis continues to worsen, hepatocytes will die, causing irreversible damage to liver functions, and it is difficult to recover even by administering current existing drugs.

SUMMARY OF THE INVENTION

A main object of the invention is to provide a c-Met regulatory composition and its use for promoting hepatic cell regeneration capable of effectively repairing damaged hepatic cells and promoting hepatic cell regeneration by regulating polygene expression related to hepatocyte cytothesis and regeneration, such as c-Met, Notch, etc., to achieve an efficacy of treating diseases related to liver damage.

A second object of the invention is to provide a c-Met regulatory composition and its use for promoting hepatic cell regeneration, which will not cause cytotoxicity to the human body or damage cells in order to achieve an efficacy of promoting the growth of hepatic cells.

In order to achieve the above objects, the invention discloses a c-Met regulatory composition with a main component comprising an effective amount of a DMB compound (4,7-Dimethoxy-5-methyl-1,3-benzodioxole) and a carrier, and the carrier can be a pharmaceutically acceptable carrier or a carrier acceptable in food industry. By administering the c-Met regulatory composition disclosed in the invention to a patient suffering from liver disease, the condition of liver damage can be effectively improved, thereby achieving an efficacy of treating liver diseases.

In one embodiment of the invention, a concentration of the DMB compound is 1.25~20 ppm.

In another embodiment of the invention, the c-Met regulatory composition further comprises an effective amount of Antrodin A, and a concentration of the Antrodin A is at least 8.75 ppm and less than 140 ppm.

In order to achieve a better liver cytothesis efficacy, a concentration ratio of DMB to Antrodin A is 1:2~1:10, wherein a concentration ratio of DMB to Antrodin A is preferably 1:5~1:10.

In another embodiment of the invention, the DMB compound or/and the Antrodin A is/are prepared as a composition for promoting hepatic cell regeneration capable of repairing damaged hepatic cells by regulating polygene expression related to hepatocyte cytothesis and regeneration, such as c-Met, Notch, etc., and reducing intracellular free radicals or oxidative stress, thereby capable of maintaining an activity of normal hepatic cells and promoting their regeneration in order to achieve an efficacy of treating diseases related to hepatic cell damage.

Wherein, a concentration of the DMB is 1.25~20 ppm; a concentration of the Antrodin A is at least 8.75 ppm and less than 140 ppm; and if both the DMB and the Antrodin A are comprised in the composition for promoting hepatic cell regeneration, a concentration ratio of DMB to Antrodin A is 1:2~1:10, and a concentration ratio of DMB to Antrodin A is preferably 1:5~1:10.

In the embodiments of the invention, the composition for promoting hepatic cell regeneration is a food, a health food or a pharmaceutical composition.

BRIEF DESCRIPTION OF THE DRAWINGS

The sole FIGURE is the result of atlas analysis of *Taiwanofungus camphoratus* mycelium powder.

DETAILED DESCRIPTION OF THE INVENTION

The invention discloses a c-Met regulatory composition with a main component comprising Antrodin A and/or DMB (4,7-Dimethoxy-5-methyl-1,3-benzodioxole) capable of effectively regulating gene expression related to cell regeneration and cytothesis in hepatic cells, such as c-Met, Notch, etc., to achieve efficacies of repairing damaged hepatic cells and promoting hepatocyte regeneration.

Wherein, c-Met and Notch are genes related to regulation pathways of hepatocyte cytothesis and regeneration respectively; when hepatocytes are stimulated by hepatotoxic drugs, an expression level of c-Met will decrease, down-regulation of c-Met will reduce the binding to its ligand HGF, thereby reducing the message transmission of hepatocyte cytothesis and regeneration; an expression level of Notch is related to hepatocyte replication, and is capable of reducing a content of ROS in hepatic cells to achieve an efficacy of protecting hepatic cells, which means that an increase in an expression level of Notch in hepatic cells is capable of achieving efficacies of promoting the proliferation of hepatic cells and improving liver damage.

Both the Antrodin A and the DMB disclosed in the invention can be prepared by chemical synthesis methods, and can also be obtained by extraction and purification from fungal mycelium. For example, when *Taiwanofungus cam-*

*phoratus* mycelium powder is analyzed by HPLC, it can be known that *Taiwanofungus camphoratus* mycelium powder comprises Antrodin A (the crest appears at the residence time of about 76-77 minutes) and DMB (the crest appears at the residence time of about 32-33 minutes), as shown in the sole FIGURE, wherein the column used is C18 (Merck Purospher STAR, 5 μm, 4.5*250 mm), flow rate 1.0 mL/min, temperature 30° C., injection volume 10 μL, detection time 120 minutes, mobile phase is 0.1% formic acid (A) and 100% acetonitrile (B), wavelength is 254 nm.

It should be noted that although the Antrodin A and the DMB are extracted and purified from *Taiwanofungus camphoratus*, the previous documents only reveal that *Taiwanofungus camphoratus* extract has toxic activity against cancer cells. However, a main efficacy of the c-Met regulatory composition disclosed in the invention lies in protecting and repairing cells, and being capable of promoting cell regeneration, which means that the c-Met regulatory composition disclosed in the invention will not be toxic to cells, let alone have the capability to kill cells with toxicity.

c-Met and Notch disclosed in the invention are genes related to regulation pathways of hepatocyte cytothesis and regeneration respectively. Specifically, when hepatocytes are stimulated by hepatotoxic drugs, an expression level of c-Met will decrease, down-regulation of c-Met will reduce the binding to its ligand HGF, thereby reducing the message transmission of hepatocyte cytothesis and regeneration; an expression level of Notch is related to hepatocyte replication, and is capable of reducing a content of ROS in hepatic cells to achieve an efficacy of protecting hepatic cells, which means that an increase in an expression level of Notch in hepatic cells is capable of achieving efficacies of promoting the proliferation of hepatic cells and improving liver damage.

Hereinafter, in order to illustrate and verify the technical features and efficacies of the invention, several examples in conjunction with tables are provided for further explanation as follows.

Cells used in the following examples are those that can be easily obtained by persons having ordinary skill in the art to which the invention pertains, so no patent deposit is required.

The Antrodin A and the DMB used in the following examples are prepared and obtained by chemical synthesis methods. Based on chemical synthesis methods being ordinary skill in the art to which the invention pertains, so they will not be mentioned here again.

Example 1: Cell Viability Analysis (1)

Normal hepatocytes of FL83B mice are divided into several groups (FL83B 1×10$^4$ cells/well), an amount of cells in each of the groups is treated under different conditions respectively and cultured for 24 hours. Then, the commercially available MTS cell viability analysis kit (CellTiter-Glo® One Solution Assay) is used to analyze the cell viability of each of the groups, the treatment condition of each of the groups of cells and the corresponding survival rate are shown in Table 1 to Table 3 below.

From the results in Table 1 below, it can be known that the Antrodin A is toxic to hepatic cells at a concentration of 140 ppm, resulting in a decrease in the survival rate of the hepatic cells, while at a concentration of 8.75 to 70 ppm, the Antrodin A is capable of effectively maintaining and enhancing the activity and survival rate of the normal hepatic cells. From the results in Table 2 below, it can be known that the addition of various concentrations of DMB not only does not cause toxicity to the normal hepatic cells, but is capable of helping the growth of the hepatic cells.

Comparing the results in Table 1 with Table 3, it can be known that under the condition of the same concentration of the Antrodin A, the survival rate of the normal hepatocytes with addition of the DMB will be higher than that of the cells only added with the Antrodin A. When a concentration of the Antrodin A is not causing cytotoxicity, addition of the DMB will help to increase cell viability, and when a concentration of the Antrodin A has caused cytotoxicity, addition of the DMB will protect the hepatic cells from cytotoxicity caused by the Antrodin A, and is capable of effectively improving cell viability and survival rate.

TABLE 1

Cell viability analysis results of normal hepatocytes cultured with different concentrations of Antrodin A

| Antrodin A dosage (ppm) | 140 | 70 | 35 | 17.5 | 8.75 |
|---|---|---|---|---|---|
| Cell viability (%, relative to the blank group) | 50.8 ± 4.4 | 108.5 ± 5.7 | 106.8 ± 6.5 | 107.1 ± 1.2 | 95.8 ± 4.8 |

TABLE 2

Cell viability analysis results of normal hepatocytes cultured with different concentrations of DMB

| DMB dosage (ppm) | 20 | 10 | 5 | 2.5 | 1.25 |
|---|---|---|---|---|---|
| Cell viability (%, relative to the blank group) | 110.6 ± 4.0 | 112.6 ± 3.4 | 115.2 ± 2.0 | 114.5 ± 1.5 | 112.0 ± 2.4 |

TABLE 3

Cell viability analysis results of normal hepatocytes cultured with different ratios of Antrodin A and DMB

| Antrodin A dosage (ppm) | 140 | 70 | 35 | 17.5 | 8.75 |
|---|---|---|---|---|---|
| DMB dosage (ppm) | 20 | 10 | 5 | 2.5 | 1.25 |
| Cell viability (%, relative to the blank group) | 54.8 ± 2.4 | 102.7 ± 1.9 | 109.5 ± 0.0 | 113.7 ± 2.9 | 113.9 ± 0.2 |

Example 2: Cell Viability Analysis (2)

Normal hepatocytes of FL83B mice are divided into several groups (FL83B 1×10$^4$ cells/well), and treated with 10 mM acetaminophen for 24 hours respectively to make the hepatic cells in a damaged state, the acetaminophen is removed and then the hepatic cells are treated with different concentrations of the Antrodin A and/or the DMB for 24 hours. Then, the commercially available MTS cell viability analysis kit (CellTiter-Glo® One Solution Assay) is used to analyze the cell viability of each of the groups, the treatment condition of each of the groups of cells and the corresponding survival rate are shown in Table 4 to Table 6 below.

From the results in Table 4 and Table 5, it can be known that addition of the Antrodin A or the DMB is capable of repairing the damaged hepatic cells and increasing the activity of the hepatic cells; and the DMB has a better efficacy of repairing the damaged hepatic cells when its concentration is lower than that of the Antrodin A.

Furthermore, from the results in Table 6, it can be known that treatment of the damaged hepatocytes with the Antrodin A and the DMB at the same time has a better cytothesis effect on the hepatocytes than those treated with the Antrodin A alone; and a concentration ratio of the DMB to the Antrodin A being 1:2~1:10 is capable of improving the activity and survival rate of the damaged hepatic cells. Wherein, a concentration ratio of the DMB to the Antrodin A being 1:5~1:10 is capable of achieving a better efficacy of repairing the damaged hepatic cells.

TABLE 4

Cell viability analysis results after treatment with different concentrations of Antrodin A

| Antrodin A dosage (ppm) | 70 | 35 | 17.5 |
|---|---|---|---|
| Cell viability (%, relative to the blank group) | 102.7 ± 3.3 | 90.2 ± 9.9 | 101.9 ± 10.7 |

TABLE 5

Cell viability analysis results after treatment with different concentrations of DMB

| DMB dosage (ppm) | 17.5 | 10 | 5 | 2.5 |
|---|---|---|---|---|
| Cell viability (%, relative to the blank group) | 103.4 ± 7.7 | 78.2 ± 8.8 | 104.1 ± 4.4 | 114.3 ± 3.9 |

TABLE 6

Cell viability analysis results after treatment with different ratios of Antrodin A and DMB

| Antrodin A dosage (ppm) | 72.7 | 70 | 66.7 | 53.33 | 35 | 17.5 |
|---|---|---|---|---|---|---|
| DMB dosage (ppm) | 7.3 | 10 | 13.3 | 26.67 | 5 | 2.5 |
| Cell viability (%, relative to the blank group) | 108.7 ± 1.3 | 118.9 ± 4.2 | 93.5 ± 3.3 | 101.0 ± 0.2 | 103.1 ± 6.4 | 107.3 ± 8.6 |

Example 3: Gene Expression Analysis

Real-time qPCR kits are used to analyze the gene expression in cells treated with different concentrations of the Antrodin A and the DMB in Example 2, and the results are shown in Tables 7 to 9 below.

From the results in Table 7 to Table 9, it can be known that both the Antrodin A and the DMB are capable of helping the damaged hepatic cells to increase the expression levels of c-Met and Notch, and achieving an efficacy of accelerating the cytothesis and regeneration of the damaged hepatic cells. If the Antrodin A and the DMB are used to treat the cells at the same time, the expression levels of c-Met and Notch in the damaged hepatic cells are significantly better than that of treating with the Antrodin A alone, indicating that the DMB has a higher capability to regulate c-Met and Notch.

TABLE 7

Results of detecting gene expression of c-Met after treatment with different ratios of Antrodin A and DMB

| Antrodin A dosage (ppm) | 72.7 | 70 | 66.7 | 53.33 | 35 | 17.5 |
|---|---|---|---|---|---|---|
| DMB dosage (ppm) | 7.3 | 10 | 13.3 | 26.67 | 5 | 2.5 |
| c-Met expression | 0.3 ± 0.3 | 6.9 ± 0.3 | 3.4 ± 0.7 | 4.8 ± 0.9 | 1.0 ± 0.4 | 0.7 ± 1.1 |

TABLE 8

Detection of Notch-2 RNA expression level after treatment with different ratios of Antrodin A and DMB

| Antrodin A dosage (ppm) | 72.7 | 70 | 66.7 | 53.33 | 35 | 17.5 |
|---|---|---|---|---|---|---|
| DMB dosage (ppm) | 7.3 | 10 | 13.3 | 26.67 | 5 | 2.5 |
| c-Met expression | 2.0 ± 0.2 | 0.7 ± 0.8 | NA | NA | 3.4 ± 0.0 | NA |

TABLE 9

Detection of HNF4a RNA expression level after treatment with different ratios of Antrodin A and DMB

| Antrodin A dosage (ppm) | 72.7 | 70 | 66.7 | 53.33 | 35 | 17.5 |
|---|---|---|---|---|---|---|
| DMB dosage (ppm) | 7.3 | 10 | 13.3 | 26.67 | 5 | 2.5 |
| c-Met expression | 0.5 ± 1.9 | 0.8 ± 0.1 | NA | NA | 1.4 ± 0.0 | NA |

In summary, the results of Examples 1 to 3 show that the c-Met regulatory composition disclosed in the invention not only has no cytotoxicity to hepatic cells, but is also capable of effectively achieving efficacies of repairing damaged hepatic cells and promoting hepatic cell regeneration. Therefore, by administering an effective amount of the c-Met regulatory composition to a patient with liver disease is capable of achieving efficacies of treating liver damage and improving liver functions.

Example 4: Verification of the Efficacy of Antiviral Drug Adjuvant

In this example, a total of 29 subjects, all suffering from chronic hepatitis B, are randomly divided into 2 groups. Wherein, the control group (n=14) is administered with the c-Met regulatory composition, but no antiviral drug entecavir is administered, and the treatment group (n=15) is administered with the antiviral drug entecavir and the c-Met regulatory composition.

The c-Met regulatory composition administered in this example comprises 614.01 ppm DMB and 3937.39 ppm Antrodin A, which means that a ratio of the Antrodin A to the DMB in the c-Met regulatory composition administered in this example is about 6.5:1. The administration period is 48 weeks, and the curative effect and virological relapse at the 12th, 24th, 36th, 48th, 60th, and 72th weeks after the start of the treatment are tested and recorded respectively, the results are shown in Table 10 and Table 11 below. And, the curative effect and relapse of patients with or without hepatitis B virus e antigen in the treatment group during treatment and after receiving treatment are further analyzed, the results are shown in Table 12. Wherein, the so-called virological relapse is defined as two consecutive hepatitis B-DNA greater than 2000 IU/mL at least 3 months after receiving nucleotide anti-hepatitis B virus drug treatment; the so-called virological relapse is defined as an increase in ALT that is more than 2 times the normal value and hepatitis B-DNA greater than 2000 IU/mL after receiving nucleotide anti-hepatitis B virus drug treatment.

In addition, blood and urine of the treatment group and the control group are collected and tested for the following: AST, ALT, bilirubin, alkaline phosphatase (ALK-P), rGT (r-glutamyl transferase), AFT (Alpha-Fetoprotein), PT (Prothrombin Time), APTT (Activated Partial Thromboplastin Time), albumin, globulin, renal BUN, creatinine, fasting blood glucose (GlucoseAC), glycated hemoglobin (HbA1c), white blood cells (leucocytes), red blood cells (erythrocytes), hemoglobin, hematocrit (HCT), red blood cell distribution width (RDW), platelets, mean corpuscular volume (MCV), mean corpuscular hemoglobin (MCH) volume, mean corpuscular hemoglobin concentration (MCHC), mean platelet volume (MPV), urine specific gravity, urine PH value, and a quantity of urinary epithelial cells, and each of the detection indices of the two groups are analyzed. The results are shown in Table 13 to Table 41.

The above results show that long-term administration of the c-Met regulatory composition disclosed in the invention will not cause adverse effects on the health of patients with viral hepatitis. In other words, the c-Met regulatory composition disclosed in the invention is indeed an effective and safe hepatoprotective adjuvant.

TABLE 10

Changes in hepatitis B virus amount of patients in the control group after receiving treatment

| | Hepatitis B-DNA not detected (person (%)) | Hepatitis B-DNA ≤ 20 IU/mL (person (%)) | Hepatitis B-DNA ≤ 1000 IU/mL (person (%)) | Hepatitis B-DNA ≤ 2000 IU/mL (person (%)) |
| --- | --- | --- | --- | --- |
| Week 12 | | | 1(7%) | 2(14%) |
| Week 24 | | | 1(7%) | 3(21%) |
| Week 36 | | 1(7%) | 1(7%) | 2(14%) |
| Week 48 | | | 2(14%) | 3(21%) |
| Week 60 | | | | 1(7%) |
| Week 72 | | 1(7%) | 3(21%) | 4(29%) |

TABLE 11

Record results of changes in hepatitis B virus amount, viral relapse, and clinical relapse of patients in the treatment group after receiving treatment

| | Hepatitis B-DNA not detected (person (%)) | Hepatitis B-DNA ≤ 20 IU/mL (person (%)) | Hepatitis B-DNA ≤ 1000 IU/mL (person (%)) | Hepatitis B-DNA ≤ 2000 IU/mL (person (%)) | Viral relapse (person (%)) | Clinical relapse (person (%)) |
| --- | --- | --- | --- | --- | --- | --- |
| Week 12 | | 5 (33%) | 13 (87%) | 10 (67%) | | |
| Week 24 | 3 (20%) | 8 (53%) | 13 (87%) | 13 (87%) | | |
| Week 36 | 3 (20%) | 11 (73%) | 12 (80%) | 13 (87%) | | |
| Week 48 | 4 (27%) | 13 (87%) | 13 (87%) | 13 (87%) | | |
| Week 60 | 1 (7%) | 5 (33%) | 8 (53%) | 8 (53%) | | 1 (6.7%) |
| Week 72 | | 2 (13%) | 5 (33%) | 5 (33%) | 9 (60%) | 1 (6.7%) |
| Relapse rate | | | | | 60% | 13.3% |

TABLE 12

Record results of changes in hepatitis B virus amount, viral relapse, and clinical relapse of hepatitis B virus e antigen-positive patients and hepatitis B virus e antigen-negative patients in the treatment group after receiving treatment

| | Hepatitis B-DNA not detected (person (%)) | Hepatitis B-DNA ≤ 20 IU/mL (person (%)) | Hepatitis B-DNA ≤ 1000 IU/mL (person (%)) | Hepatitis B-DNA ≤ 2000 IU/mL (person (%)) | Viral relapse (person (%)) | Clinical relapse (person (%)) |
|---|---|---|---|---|---|---|
| Hepatitis B virus e antigen positive (n = 4) | | | | | | |
| Week 12 | | 1 (25%) | 2 (50%) | | | |
| Week 24 | 1 (25%) | | 2 (50%) | | | |
| Week 36 | 1 (25%) | 1 (25%) | 1 (25%) | | | |
| Week 48 | 1 (25%) | 2 (50%) | | | | |
| Week 60 | | | 1 (25%) | | | |
| Week 72 | | 1 (25%) | 1 (25%) | | 2 (50%) | 0 (0%) |
| Relapse rate | | | | | 50% | 0 (0%) |
| Hepatitis B virus e antigen negative (n = 11) | | | | | | |
| Week 12 | — | 5 (45%) | 5 (45%) | | — | — |
| Week 24 | 3 (27%) | 5 (45%) | 2 (18%) | | — | — |
| Week 36 | 3 (27%) | 7 (64%) | | | — | — |
| Week 48 | 4 (36%) | 6 (55%) | | | — | — |
| Week 60 | 1 (9%) | 3 (27%) | 3 (27%) | | — | 1 (9.09%) |
| Week 72 | — | 1 (9% | 3 (27%) | | 5 (45.2%) | 1 (9.09%) |
| Relapse rate | | | | | 45.5% | 18.2% |

TABLE 13

Analysis of AST in the treatment group and the control group

| | Control group | Treatment group | P value |
|---|---|---|---|
| Week 0 | 56.36 ± 21.25 | 59.33 ± 35.17 | 0.79 |
| Week 48 | 38.57 ± 14.91 | 25.07 ± 5.51 | 0.006 |
| Week 60 | 50.00 ± 42.38 | 29.00 ± 9.33 | 0.09 |
| Week 72 | 48.00 ± 44.42 | 35.2 ± 21.68 | 0.34 |
| Week 48-Week 0 | −17.79 ± 20.77 | −34.27 ± 34.71 | 0.14 |
| Week 60-Week 0 | −6.36 ± 35.79 | −30.33 ± 35.57 | 0.08 |
| Week 72-Week 0 | −8.36 ± 52.17 | −24.13 ± 42.05 | 0.38 |
| Week 60-Week 48 | 11.43 ± 41.63 | 3.93 ± 7.87 | 0.52 |
| Week 72-Week 48 | 9.43 ± 44.62 | 10.13 ± 22.08 | 0.96 |
| Week 72-Week 60 | −2.00 ± 65.62 | 6.20 ± 16.90 | 0.66 |

TABLE 14

Analysis of ALT in the treatment group and the control group

| | Control group | Treatment group | P value |
|---|---|---|---|
| Week 0 | 88.21 ± 47.02 | 107.27 ± 82.81 | 0.45 |
| Week 48 | 48.50 ± 17.68 | 26.13 ± 8.18 | <0.001 |
| Week 60 | 68.21 ± 71.75 | 35.13 ± 21.40 | 0.12 |
| Week 72 | 80.00 ± 132.30 | 42.27 ± 44.56 | 0.39 |
| Week 48-Week 0 | −39.71 ± 43.78 | −81.13 ± 82.24 | 0.10 |
| Week 60-Week 0 | −20.00 ± 56.60 | −72.13 ± 84.49 | 0.06 |
| Week 72-Week 0 | −8.21 ± 139.57 | −60.00 ± 98.74 | 0.26 |
| Week 60-Week 48 | 19.71 ± 71.83 | 9.00 ± 17.75 | 0.60 |
| Week 72-Week 48 | 31.50 ± 130.84 | 21.13 ± 43.87 | 0.78 |
| Week 72-Week 60 | 11.79 ± 158.47 | 12.13 ± 36.61 | 0.99 |

TABLE 15

Analysis of total bilirubin and direct bilirubin in the treatment group and the control group

| | Control group | Treatment group | P value |
|---|---|---|---|
| Total bilirubin | | | |
| Week 0 | 0.98 ± 0.46 | 0.88 ± 0.26 | 0.49 |
| Week 48 | 0.98 ± 0.31 | 0.91 ± 0.32 | 0.59 |
| Week 60 | 0.69 ± 0.24 | 0.75 ± 0.28 | 0.58 |
| Week 72 | 0.96 ± 0.25 | 0.86 ± 0.37 | 0.44 |
| Week 48-Week 0 | 0.00 ± 0.33 | 0.03 ± 0.26 | 0.76 |
| Week 60-Week 0 | −0.29 ± 0.29 | −0.13 ± 0.20 | 0.10 |
| Week 72-Week 0 | −0.02 ± 0.37 | −0.02 ± 0.37 | 0.97 |
| Week 60-Week 48 | −0.29 ± 0.25 | −0.17 ± 0.30 | 0.26 |
| Week 72-Week 60 | −0.02 ± 0.29 | −0.05 ± 0.33 | 0.81 |
| Week 72-Week 48 | 0.26 ± 0.24 | 0.12 ± 0.36 | 0.21 |
| Direct bilirubin | | | |
| Week 0 | 0.14 ± 0.06 | 0.14 ± 0.06 | 0.91 |
| Week 48 | 0.14 ± 0.06 | 0.13 ± 0.05 | 0.66 |
| Week 60 | 0.11 ± 0.04 | 0.17 ± 0.23 | 0.35 |
| Week 72 | 0.14 ± 0.05 | 0.12 ± 0.06 | 0.58 |
| Week 48-Week 0 | −0.01 ± 0.03 | −0.01 ± 0.06 | 0.73 |

TABLE 15-continued

Analysis of total bilirubin and direct bilirubin in the treatment group and the control group

|  | Control group | Treatment group | P value |
|---|---|---|---|
| Week 60-Week 0 | −0.03 ± 0.05 | 0.03 ± 0.24 | 0.35 |
| Week 72-Week 0 | −0.01 ± 0.06 | −0.02 ± 0.06 | 0.72 |
| Week 60-Week 48 | −0.02 ± 0.04 | 0.05 ± 0.24 | 0.30 |
| Week 72-Week 48 | 0.00 ± 0.06 | 0.00 ± 0.04 | 0.91 |
| Week 72-Week 60 | 0.02 ± 0.04 | −0.05 ± 0.24 | 0.28 |

TABLE 16

Analysis of ALK-P in the treatment group and the control group

|  | Control group | Treatment group | P value |
|---|---|---|---|
| Week 0 | 72.07 ± 27.33 | 62.80 ± 15.20 | 0.28 |
| Week 48 | 76.71 ± 35.35 | 56.79 ± 19.25 | 0.08 |
| Week 60 | 79.07 ± 35.79 | 61.40 ± 14.84 | 0.10 |
| Week 72 | 71.14 ± 35.63 | 59 ± 14.03 | 0.25 |
| Week 48-Week 0 | 4.64 ± 8.88 | −6.01 ± 2.15 | 0.01 |
| Week 60-Week 0 | 7.00 ± 13.67 | −1.40 ± 11.88 | 0.09 |
| Week 72-Week 0 | −0.93 ± 21.25 | −3.80 ± 12.8 | 0.66 |
| Week 60-Week 48 | 2.36 ± 12.98 | 4.61 ± 12.51 | 0.64 |
| Week 72-Week 48 | −5.57 ± 23.45 | 2.21 ± 15.27 | 0.30 |
| Week 72-Week 60 | −7.93 ± 18.00 | −2.40 ± 4.58 | 0.28 |

TABLE 17

Analysis of γ-GT in the treatment group and the control group

|  | Control group | Treatment group | P value |
|---|---|---|---|
| Week 0 | 30.79 ± 18.55 | 28.47 ± 14.43 | 0.71 |
| Week 48 | 24.21 ± 8.82 | 19.47 ± 19.17 | 0.40 |
| Week 60 | 24.86 ± 9.97 | 20.13 ± 16.76 | 0.37 |
| Week 72 | 24.86 ± 10.58 | 18.33 ± 10.31 | 0.10 |
| Week 48-Week 0 | −6.57 ± 18.87 | −9.00 ± 14.05 | 0.70 |
| Week 60-Week 0 | −5.93 ± 19.41 | −8.33 ± 12.47 | 0.69 |
| Week 72-Week 0 | −5.93 ± 11.47 | −10.13 ± 12.36 | 0.35 |
| Week 60-Week 48 | 0.64 ± 5.34 | 0.67 ± 5.67 | 0.99 |
| Week 72-Week 48 | 0.64 ± 9.00 | −1.13 ± 9.88 | 0.62 |
| Week 72-Week 60 | 0.00 ± 10.08 | −1.80 ± 7.57 | 0.59 |

TABLE 18

Analysis of AFP in the treatment group and the control group

|  | Control group | Treatment group | P value |
|---|---|---|---|
| Week 0 | 3.45 ± 1.62 | 3.32 ± 1.48 | 0.83 |
| Week 48 | 3.21 ± 1.65 | 2.62 ± 0.83 | 0.24 |
| Week 60 | 3.24 ± 1.46 | 2.67 ± 0.82 | 0.21 |

TABLE 18-continued

Analysis of AFP in the treatment group and the control group

|  | Control group | Treatment group | P value |
|---|---|---|---|
| Week 72 | 3.46 ± 1.61 | 2.66 ± 0.90 | 0.12 |
| Week 48-Week 0 | −0.24 ± 1.08 | −0.70 ± 1.04 | 0.24 |
| Week 60-Week 0 | −0.20 ± 1.13 | −0.65 ± 1.22 | 0.32 |
| Week 72-Week 0 | 0.01 ± 1.32 | −0.67 ± 1.15 | 0.15 |
| Week 60-Week 48 | 0.03 ± 0.37 | 0.05 ± 0.60 | 0.91 |
| Week 72-Week 48 | 0.25 ± 0.98 | 0.04 ± 0.56 | 0.48 |
| Week 72-Week 60 | 0.22 ± 0.81 | −0.02 ± 0.36 | 0.33 |

TABLE 19

Analysis of PT in the treatment group and the control group

|  | Control group | Treatment group | P value |
|---|---|---|---|
| Week 0 | 10.56 ± 0.46 | 10.69 ± 0.33 | 0.37 |
| Week 48 | 10.5 ± 0.49 | 10.49 ± 0.36 | 0.93 |
| Week 60 | 10.41 ± 0.47 | 10.47 ± 0.39 | 0.75 |
| Week 72 | 10.62 ± 0.54 | 10.60 ± 0.35 | 0.90 |
| Week 48-Week 0 | −0.06 ± 0.33 | −0.21 ± 0.35 | 0.25 |
| Week 60-Week 0 | −0.14 ± 0.30 | −0.23 ± 0.42 | 0.55 |
| Week 72-Week 0 | 0.06 ± 0.34 | −0.09 ± 0.46 | 0.31 |
| Week 60-Week 48 | −0.09 ± 0.39 | −0.02 ± 0.35 | 0.64 |
| Week 72-Week 48 | 0.12 ± 0.29 | 0.11 ± 0.35 | 0.95 |
| Week 72-Week 60 | 0.21 ± 0.40 | 0.13 ± 0.41 | 0.63 |

TABLE 20

Analysis of APTT in the treatment group and the control group

|  | Control group | Treatment group | P value |
|---|---|---|---|
| Week 0 | 28.15 ± 2.83 | 27.77 ± 2.05 | 0.68 |
| Week 48 | 27.21 ± 1.00 | 27.52 ± 2.10 | 0.61 |
| Week 60 | 26.86 ± 0.88 | 27.39 ± 2.08 | 0.38 |
| Week 72 | 27.5 ± 1.13 | 27.73 ± 2.08 | 0.71 |
| Week 48-Week 0 | −0.94 ± 2.90 | −0.25 ± 1.62 | 0.44 |
| Week 60-Week 0 | −1.29 ± 2.61 | −0.37 ± 1.71 | 0.27 |
| Week 72-Week 0 | −0.65 ± 2.72 | −0.03 ± 1.73 | 0.47 |
| Week 60-Week 48 | −0.34 ± 0.69 | −0.13 ± 0.85 | 0.46 |
| Week 72-Week 48 | 0.29 ± 0.69 | 0.21 ± 0.76 | 0.77 |
| Week 72-Week 60 | 0.64 ± 0.80 | 0.34 ± 0.93 | 0.37 |

TABLE 21

Analysis of albumin in the treatment group and the control group

|  | Control group | Treatment group | P value |
|---|---|---|---|
| Week 0 | 4.48 ± 0.23 | 4.60 ± 0.24 | 0.17 |
| Week 48 | 4.59 ± 0.28 | 4.63 ± 0.22 | 0.72 |

TABLE 21-continued

Analysis of albumin in the treatment group and the control group

|  | Control group | Treatment group | P value |
|---|---|---|---|
| Week 60 | 4.51 ± 0.28 | 4.61 ± 0.25 | 0.36 |
| Week 72 | 4.59 ± 0.24 | 4.67 ± 0.25 | 0.39 |
| Week 48-Week 0 | 0.114 ± 0.29 | 0.03 ± 0.25 | 0.40 |
| Week 60-Week 0 | 0.04 ± 0.26 | 0.01 ± 0.36 | 0.81 |
| Week 72-Week 0 | 0.11 ± 0.28 | 0.07 ± 0.40 | 0.76 |
| Week 60-Week 48 | −0.08 ± 0.30 | −0.02 ± 0.21 | 0.55 |
| Week 72-Week 48 | −0.01 ± 0.20 | 0.04 ± 0.26 | 0.59 |
| Week 72-Week 60 | 0.07 ± 0.30 | 0.06 ± 0.19 | 0.90 |

TABLE 22

Analysis of globulin in the treatment group and the control group

|  | Control group | Treatment group | P value |
|---|---|---|---|
| Week 0 | 2.69 ± 0.41 | 2.72 ± 0.28 | 0.79 |
| Week 48 | 2.64 ± 0.43 | 2.65 ± 0.26 | 0.98 |
| Week 60 | 2.71 ± 0.51 | 2.61 ± 0.25 | 0.51 |
| Week 72 | 2.59 ± 0.54 | 2.66 ± 0.23 | 0.67 |
| Week 48-Week 0 | −0.04 ± 0.21 | −0.07 ± 0.31 | 0.76 |
| Week 60-Week 0 | 0.03 ± 0.22 | −0.11 ± 0.28 | 0.17 |
| Week 72-Week 0 | −0.09 ± 0.27 | −0.06 ± 0.23 | 0.73 |
| Week 60-Week 48 | 0.07 ± 0.26 | −0.03 ± 0.31 | 0.34 |
| Week 72-Week 48 | −0.05 ± 0.37 | 0.01 ± 0.20 | 0.57 |
| Week 72-Week 60 | −0.12 ± 0.32 | 0.05 ± 0.31 | 0.16 |

TABLE 23

Analysis of renal BUN in the treatment group and the control group

|  | Control group | Treatment group | P value |
|---|---|---|---|
| Week 0 | 10.62 ± 2.66 | 13.20 ± 2.98 | 0.02 |
| Week 48 | 11.79 ± 3.21 | 13.13 ± 3.07 | 0.26 |
| Week 60 | 11.36 ± 2.37 | 12.93 ± 3.28 | 0.15 |
| Week 72 | 11.36 ± 2.47 | 12.73 ± 3.10 | 0.20 |
| Week 48-Week 0 | 0.69 ± 2.72 | −0.07 ± 3.56 | 0.54 |
| Week 60-Week 0 | 0.62 ± 3.01 | −0.27 ± 2.99 | 0.44 |
| Week 72-Week 0 | 0.77 ± 2.49 | −0.47 ± 3.04 | 0.25 |
| Week 60-Week 48 | −0.43 ± 2.53 | −0.20 ± 2.24 | 0.80 |
| Week 72-Week 48 | −0.43 ± 3.52 | −0.40 ± 2.80 | 0.98 |
| Week 72-Week 60 | 0.00 ± 3.49 | −0.20 ± 3.12 | 0.87 |

TABLE 24

Analysis of renal creatinine in the treatment group and the control group

|  | Control group | Treatment group | P value |
|---|---|---|---|
| Week 0 | 0.80 ± 0.16 | 1.00 ± 0.19 | 0.005 |
| Week 48 | 0.76 ± 0.17 | 0.96 ± 0.18 | 0.006 |
| Week 60 | 0.78 ± 0.20 | 0.97 ± 0.17 | 0.01 |
| Week 72 | 0.75 ± 0.20 | 0.94 ± 0.18 | 0.01 |
| Week 48-Week 0 | −0.03 ± 0.09 | −0.04 ± 0.08 | 0.58 |
| Week 60-Week 0 | −0.01 ± 0.08 | −0.03 ± 0.10 | 0.64 |
| Week 72-Week 0 | −0.03 ± 0.08 | −0.07 ± 0.09 | 0.28 |
| Week 60-Week 48 | 0.01 ± 0.08 | 0.01 ± 0.09 | 0.99 |
| Week 72-Week 48 | −0.01 ± 0.09 | −0.02 ± 0.07 | 0.79 |
| Week 72-Week 60 | −0.03 ± 0.08 | −0.04 ± 0.12 | 0.82 |

TABLE 25

Analysis of fasting blood glucose in the treatment group and the control group

|  | Control group | Treatment group | P value |
|---|---|---|---|
| Week 0 | 99.1 ± 19.69 | 94.88 ± 7.22 | 0.60 |
| Week 48 | 102.00 ± 13.48 | 93.13 ± 7.08 | 0.13 |
| Week 72 | 99.29 ± 12.97 | 92.5 ± 4.9 | 0.23 |
| Week 48-Week 0 | 2.86 ± 8.4 | −1.75 ± 7.25 | 0.27 |
| Week 60-Week 0 | 0.14 ± 10.95 | −2.38 ± 5.63 | 0.58 |
| Week 72-Week 48 | −2.71 ± 5.77 | −0.63 ± 4.81 | 0.46 |

TABLE 26

Analysis of glycated hemoglobin in the treatment group and the control group

|  | Control group | Treatment group | P value |
|---|---|---|---|
| Week 0 | 5.94 ± 0.50 | 5.48 ± 0.18 | 0.05 |
| Week 48 | 5.83 ± 0.52 | 5.40 ± 0.18 | 0.07 |
| Week 72 | 5.98 ± 0.5 | 5.56 ± 0.18 | 0.15 |
| Week 48-Week 0 | −0.11 ± 0.2 | −0.08 ± 0.12 | 0.64 |
| Week 60-Week 0 | −0.06 ± 0.26 | 0.09 ± 0.11 | 0.21 |
| Week 72-Week 48 | 0.06 ± 0.14 | 0.16 ± 0.14 | 0.17 |

TABLE 27

Analysis of white blood cell content in the blood of the treatment group and the control group

|  | Control group | Treatment group | P value |
|---|---|---|---|
| Week 0 | 6.79 ± 1.06 | 6.53 ± 1.6 | 0.61 |
| Week 48 | 6.56 ± 0.85 | 5.91 ± 1.46 | 0.16 |
| Week 60 | 7.14 ± 1.47 | 6.59 ± 1.66 | 0.36 |
| Week 72 | 6.18 ± 0.91 | 5.91 ± 1.30 | 0.52 |
| Week 48-Week 0 | −0.23 ± 1.42 | −0.61 ± 1.35 | 0.46 |
| Week 60-Week 0 | 0.35 ± 1.50 | 0.06 ± 1.22 | 0.57 |
| Week 72-Week 0 | −0.61 ± 0.68 | −0.62 ± 1.36 | 0.97 |

TABLE 27-continued

Analysis of white blood cell content in the blood of the treatment group and the control group

|  | Control group | Treatment group | P value |
|---|---|---|---|
| Week 60-Week 48 | 0.58 ± 1.49 | 0.67 ± 1.07 | 0.84 |
| Week 72-Week 48 | −0.38 ± 1.12 | −0.01 ± 0.88 | 0.33 |
| Week 72-Week 60 | −0.96 ± 1.57 | −0.68 ± 1.03 | 0.58 |

TABLE 28

Analysis of red blood cell content in the blood of the treatment group and the control group

|  | Control group | Treatment group | P value |
|---|---|---|---|
| Week 0 | 4.84 ± 0.32 | 4.93 ± 0.39 | 0.48 |
| Week 48 | 4.9 ± 0.41 | 4.92 ± 0.33 | 0.87 |
| Week 60 | 4.57 ± 1.04 | 4.90 ± 0.40 | 0.29 |
| Week 72 | 4.82 ± 0.36 | 4.98 ± 0.29 | 0.19 |
| Week 48-Week 0 | 0.07 ± 0.20 | −0.01 ± 0.17 | 0.31 |
| Week 60-Week 0 | −0.26 ± 0.90 | −0.03 ± 0.28 | 0.34 |
| Week 72-Week 0 | −0.02 ± 0.13 | 0.05 ± 0.23 | 0.37 |
| Week 60-Week 48 | −0.33 ± 0.88 | −0.02 ± 0.17 | 0.22 |
| Week 72-Week 48 | −0.08 ± 0.17 | 0.06 ± 0.20 | 0.06 |
| Week 72-Week 60 | 0.25 ± 0.88 | 0.08 ± 0.27 | 0.50 |

TABLE 29

Analysis of hemoglobin content in the blood of the treatment group and the control group

|  | Control group | Treatment group | P value |
|---|---|---|---|
| Week 0 | 14.79 ± 1.25 | 15.17 ± 1.15 | 0.40 |
| Week 48 | 15.06 ± 1.31 | 15.14 ± 1.12 | 0.86 |
| Week 60 | 14.76 ± 1.11 | 15.01 ± 1.17 | 0.57 |
| Week 72 | 14.79 ± 1.09 | 15.31 ± 1.14 | 0.22 |
| Week 48-Week 0 | 0.26 ± 0.51 | −0.03 ± 0.51 | 0.13 |
| Week 60-Week 0 | −0.03 ± 0.53 | −0.17 ± 0.77 | 0.58 |
| Week 72-Week 0 | −0.01 ± 0.30 | 0.13 ± 0.64 | 0.45 |
| Week 60-Week 48 | −0.29 ± 0.65 | −0.13 ± 0.59 | 0.49 |
| Week 72-Week 48 | −0.27 ± 0.46 | 0.17 ± 0.66 | 0.05 |
| Week 72-Week 60 | 0.02 ± 0.51 | 0.30 ± 0.71 | 0.24 |

TABLE 30

Analysis of hematocrit in the treatment group and the control group

|  | Control group | Treatment group | P value |
|---|---|---|---|
| Week 0 | 44.04 ± 3.11 | 44.89 ± 3.47 | 0.49 |
| Week 48 | 44.47 ± 3.93 | 44.37 ± 2.97 | 0.94 |
| Week 60 | 43.19 ± 3.14 | 43.99 ± 3.44 | 0.52 |
| Week 72 | 43.89 ± 3.66 | 45.03 ± 3.32 | 0.39 |
| Week 48-Week 0 | 0.44 ± 1.64 | −0.53 ± 1.43 | 0.10 |
| Week 60-Week 0 | −0.85 ± 1.51 | −0.9 ± 2.29 | 0.95 |
| Week 72-Week 0 | −0.14 ± 1.51 | 0.13 ± 2.08 | 0.69 |
| Week 60-Week 48 | −1.29 ± 2.04 | −0.37 ± 1.62 | 0.19 |
| Week 72-Week 48 | −0.58 ± 1.14 | 0.66 ± 2.00 | 0.07 |
| Week 72-Week 60 | 0.71 ± 2.23 | 1.03 ± 2.38 | 0.71 |

TABLE 31

Analysis of red blood cell distribution width in the blood of the treatment group and the control group

|  | Control group | Treatment group | P value |
|---|---|---|---|
| Week 0 | 13.37 ± 0.71 | 13.41 ± 0.45 | 0.87 |
| Week 48 | 13.35 ± 0.61 | 13.41 ± 0.47 | 0.76 |
| Week 60 | 13.37 ± 0.55 | 13.29 ± 0.55 | 0.68 |
| Week 72 | 13.29 ± 0.71 | 13.23 ± 0.49 | 0.79 |
| Week 48-Week 0 | −0.02 ± 0.37 | 0.01 ± 0.32 | 0.83 |
| Week 60-Week 0 | 0.00 ± 0.45 | −0.12 ± 0.38 | 0.44 |
| Week 72-Week 0 | −0.08 ± 0.68 | −0.17 ± 0.29 | 0.63 |
| Week 60-Week 48 | 0.02 ± 0.44 | −0.13 ± 0.40 | 0.36 |
| Week 72-Week 48 | −0.06 ± 0.44 | −0.18 ± 0.27 | 0.37 |
| Week 72-Week 60 | −0.08 ± 0.63 | −0.05 ± 0.24 | 0.89 |

TABLE 32

Analysis of platelet content in the blood of the treatment group and the control group

|  | Control group | Treatment group | P value |
|---|---|---|---|
| Week 0 | 219.36 ± 28.73 | 194.27 ± 48.03 | 0.10 |
| Week 48 | 215.71 ± 43.17 | 193.87 ± 49.96 | 0.22 |
| Week 60 | 235.71 ± 48.18 | 182.09 ± 63.24 | 0.02 |
| Week 72 | 220.14 ± 44.90 | 195.00 ± 48.10 | 0.16 |
| Week 48-Week 0 | −3.64 ± 26.82 | −0.40 ± 22.41 | 0.73 |
| Week 60-Week 0 | 16.36 ± 44.33 | −12.17 ± 61.57 | 0.17 |
| Week 72-Week 0 | 0.79 ± 28.99 | 0.73 ± 16.23 | 1.00 |
| Week 60-Week 48 | 20.00 ± 40.31 | −11.77 ± 55.93 | 0.09 |
| Week 72-Week 48 | 4.43 ± 19.75 | 1.13 ± 20.97 | 0.67 |
| Week 72-Week 60 | −15.57 ± 49.19 | 12.91 ± 63.50 | 0.19 |

TABLE 33

Analysis of mean corpuscular volume in the blood of the treatment group and the control group

|  | Control group | Treatment group | P value |
|---|---|---|---|
| Week 0 | 90.36 ± 3.95 | 91.11 ± 2.48 | 0.54 |
| Week 48 | 90.47 ± 3.28 | 90.13 ± 2.63 | 0.58 |

TABLE 33-continued

Analysis of mean corpuscular volume in the blood of the treatment group and the control group

|  | Control group | Treatment group | P value |
|---|---|---|---|
| Week 60 | 89.88 ± 3.08 | 89.83 ± 2.88 | 0.96 |
| Week 72 | 90.97 ± 2.85 | 90.32 ± 3.23 | 0.57 |
| Week 48-Week 0 | 0.38 ± 2.40 | −0.99 ± 1.05 | 0.07 |
| Week 60-Week 0 | −0.49 ± 2.84 | −1.29 ± 0.90 | 0.33 |
| Week 72-Week 0 | 0.61 ± 2.18 | −0.79 ± 1.60 | 0.06 |
| Week 60-Week 48 | −0.86 ± 0.95 | −0.30 ± 0.93 | 0.12 |
| Week 72-Week 48 | 0.23 ± 1.41 | 0.19 ± 1.49 | 0.95 |
| Week 72-Week 60 | 1.09 ± 1.55 | 0.49 ± 1.08 | 0.23 |

TABLE 34

Analysis of mean corpuscular hemoglobin volume in the blood of the treatment group and the control group

|  | Control group | Treatment group | P value |
|---|---|---|---|
| Week 0 | 30.57 ± 1.50 | 30.80 ± 1.04 | 0.64 |
| Week 48 | 30.71 ± 1.16 | 30.78 ± 1.07 | 0.88 |
| Week 60 | 30.69 ± 1.16 | 30.64 ± 1.12 | 0.90 |
| Week 72 | 30.71 ± 1.05 | 30.69 ± 1.18 | 0.96 |
| Week 48-Week 0 | 0.14 ± 0.84 | −0.02 ± 0.55 | 0.54 |
| Week 60-Week 0 | 0.12 ± 0.73 | −0.16 ± 0.52 | 0.24 |
| Week 72-Week 0 | 0.14 ± 0.83 | −0.11 ± 0.65 | 0.37 |
| Week 60-Week 48 | −0.02 ± 0.31 | −0.14 ± 0.56 | 0.48 |
| Week 72-Week 48 | −0.01 ± 0.48 | −0.09 ± 0.63 | 0.68 |
| Week 72-Week 60 | 0.01 ± 0.51 | 0.05 ± 0.62 | 0.88 |

TABLE 35

Analysis of mean corpuscular hemoglobin in the blood of the treatment group and the control group

|  | Control group | Treatment group | P value |
|---|---|---|---|
| Week 0 | 33.54 ± 0.88 | 33.82 ± .67 | 0.35 |
| Week 48 | 33.84 ± 0.40 | 34.12 ± 0.68 | 0.20 |
| Week 60 | 34.17 ± 0.65 | 34.10 ± 0.44 | 0.73 |
| Week 72 | 33.74 ± 0.52 | 33.99 ± 0.63 | 0.26 |
| Week 48-Week 0 | 0.30 ± 0.99 | 0.30 ± 0.53 | 1.00 |
| Week 60-Week 0 | 0.63 ± 0.71 | 0.28 ± 0.58 | 0.15 |
| Week 72-Week 0 | 0.20 ± 1.05 | 0.17 ± 0.70 | 0.94 |
| Week 60-Week 48 | 0.33 ± 0.50 | −0.02 ± 0.66 | 0.12 |
| Week 72-Week 48 | −0.10 ± 0.64 | −0.13 ± 0.77 | 0.92 |
| Week 72-Week 60 | −0.43 ± 0.79 | −0.11 ± 0.58 | 0.22 |

TABLE 36

Analysis of mean platelet volume in the blood of the treatment group and the control group

|  | Control group | Treatment group | P value |
|---|---|---|---|
| Week 0 | 8.08 ± 0.64 | 8.15 ± 0.81 | 0.80 |
| Week 48 | 8.19 ± 0.67 | 8.04 ± 0.69 | 0.57 |
| Week 60 | 7.92 ± 0.63 | 8.02 ± 0.85 | 0.73 |
| Week 72 | 8.05 ± 0.70 | 8.07 ± 0.75 | 0.95 |
| Week 48-Week 0 | 0.11 ± 0.40 | −0.11 ± 0.39 | 0.16 |
| Week 60-Week 0 | −0.16 ± 0.43 | −0.13 ± 0.37 | 0.84 |
| Week 72-Week 0 | −0.03 ± 0.46 | −0.08 ± 0.32 | 0.73 |
| Week 60-Week 48 | −0.26 ± 0.48 | −0.02 ± 0.31 | 0.11 |
| Week 72-Week 48 | −0.14 ± 0.32 | 0.03 ± 0.25 | 0.13 |
| Week 72-Week 60 | 0.13 ± 0.50 | 0.05 ± 0.32 | 0.60 |

TABLE 37

Comparison of urine specific gravity between the treatment group and the control group

|  | Control group | Treatment group | P value |
|---|---|---|---|
| Week 0 | 1.02 ± 0.01 | 1.02 ± 0.01 | 0.59 |
| Week 48 | 1.02 ± 0.00 | 1.01 ± 0.01 | 0.31 |
| Week 60 | 1.02 ± 0.00 | 1.01 ± 0.01 | 0.03 |
| Week 72 | 1.02 ± 0.01 | 1.01 ± 0.01 | 0.32 |
| Week 48-Week 0 | 0.00 ± 0.00 | −0.002 ± 0.01 | 0.53 |
| Week 60-Week 0 | −0.001 ± 0.01 | −0.004 ± 0.01 | 0.18 |
| Week 72-Week 0 | −0.001 ± 0.01 | −0.003 ± 0.01 | 0.60 |
| Week 60-Week 48 | 0.00 ± 0.00 | −0.002 ± 0.01 | 0.40 |
| Week 72-Week 48 | −0.001 ± 0.01 | −0.001 ± 0.01 | 0.93 |
| Week 72-Week 60 | −0.001 ± 0.01 | 0.001 ± 0.01 | 0.54 |

TABLE 38

Comparison of urine PH value between the treatment group and the control group

|  | Control group | Treatment group | P value |
|---|---|---|---|
| Week 0 | 6.36 ± 0.60 | 6.30 ± 0.56 | 0.79 |
| Week 48 | 6.43 ± 0.70 | 6.30 ± 0.65 | 0.61 |
| Week 60 | 6.50 ± 0.83 | 6.10 ± 0.66 | 0.16 |
| Week 72 | 6.04 ± 0.63 | 6.23 ± .65 | 0.42 |
| Week 48-Week 0 | 0.07 ± 0.94 | 0.00 ± 0.60 | 0.81 |
| Week 60-Week 0 | 0.14 ± 0.79 | −0.2 ± 0.75 | 0.24 |
| Week 72-Week 0 | −0.32 ± 0.72 | −0.07 ± 0.86 | 0.40 |
| Week 60-Week 48 | 0.07 ± 1.28 | −0.2 ± 0.68 | 0.49 |
| Week 72-Week 48 | −0.39 ± 1.00 | −0.07 ± 0.70 | 0.32 |
| Week 72-Week 60 | −0.46 ± 0.97 | 0.13 ± 0.67 | 0.06 |

TABLE 39

Comparison of red blood cells in urine between the treatment group and the control group

| | Control group | Treatment group | P value |
|---|---|---|---|
| Week 0 | 7.00 ± 7.30 | 3.33 ± 6.16 | 0.15 |
| Week 48 | 70.93 ± 239.04 | 6.47 ± 12.60 | 0.33 |
| Week 60 | 4.71 ± 3.83 | 6.60 ± 8.58 | 0.45 |
| Week 72 | 3.50 ± 3.55 | 2.93 ± 2.66 | 0.63 |
| Week 48-Week 0 | 63.93 ± 237.89 | 3.13 ± 7.55 | 0.36 |
| Week 60-Week 0 | −2.29 ± 7.06 | 3.27 ± 8.27 | 0.06 |
| Week 72-Week 0 | −3.50 ± 6.30 | −0.40 ± 6.25 | 0.19 |
| Week 60-Week 48 | −66.21 ± 240.09 | 0.13 ± 12.09 | 0.32 |
| Week 72-Week 48 | −67.43 ± 236.59 | −3.53 ± 13.02 | 0.33 |
| Week 72-Week 60 | −1.21 ± 5.45 | −3.67 ± 8.35 | 0.36 |

TABLE 40

Comparison of white blood cells in urine between the treatment group and the control group

| | Control group | Treatment group | P value |
|---|---|---|---|
| Week 0 | 11.86 ± 28.87 | 1.93 ± 2.71 | 0.22 |
| Week 48 | 7.64 ± 14.40 | 1.67 ± 1.11 | 0.15 |
| Week 60 | 60.43 ± 209.49 | 1.33 ± 1.29 | 0.31 |
| Week 72 | 4.79 ± 6.67 | 2.2 ± 2.34 | 0.19 |
| Week 48-Week 0 | −4.21 ± 15.81 | −0.27 ± 3.06 | 0.37 |
| Week 60-Week 0 | 48.57 ± 212.06 | −0.60 ± 3.00 | 0.40 |
| Week 72-Week 0 | −7.07 ± 28.14 | 0.27 ± 2.66 | 0.35 |
| Week 60-Week 48 | 52.79 ± 12.76 | −0.33 ± 1.18 | 0.36 |
| Week 72-Week 48 | −2.86 ± 12.76 | 0.53 ± 2.29 | 0.34 |
| Week 72-Week 60 | −55.64 ± 210.63 | 0.87 ± 2.36 | 0.33 |

TABLE 41

Comparison of urinary epithelial cells between the treatment group and the control group

| | Control group | Treatment group | P value |
|---|---|---|---|
| Week 0 | 5.79 ± 9.23 | 0.73 ± 1.67 | 0.06 |
| Week 48 | 1.36 ± 1.98 | 0.27 ± 1.03 | 0.08 |
| Week 60 | 3.64 ± 10.85 | 0.13 ± 0.35 | 0.25 |
| Week 72 | 0.71 ± 1.90 | 1.00 ± 2.33 | 0.72 |
| Week 48-Week 0 | −4.43 ± 8.01 | −0.47 ± 0.92 | 0.09 |
| Week 60-Week 0 | −2.14 ± 11.04 | −0.60 ± 1.59 | 0.61 |
| Week 72-Week 0 | −5.07 ± 8.06 | 0.27 ± 0.80 | 0.03 |
| Week 60-Week 48 | 2.29 ± 9.53 | −0.13 ± 1.13 | 0.36 |
| Week 72-Week 48 | −0.64 ± 2.62 | 0.73 ± 1.58 | 0.10 |
| Week 72-Week 60 | −2.93 ± 11.27 | 0.87 ± 2.23 | 0.24 |

It is to be understood that the above description is only the embodiments and examples of the invention and is not used to limit the present invention, and changes in accordance with the concepts of the present invention may be made without departing from the spirit of the present invention. For example, the equivalent effects produced by various transformations, variations, modifications and applications made to the configurations or arrangements shall still fall within the scope covered by the appended claims of the present invention.

What is claimed is:

1. A method of promoting hepatocyte regeneration and cytothesis and protecting normal hepatic cells in a patient with liver disease comprising administering to a patient in need thereof an effective amount of c-Met regulatory composition, wherein the c-Met regulatory composition comprises 4,7-dimethoxy-5-methyl-1,3-benzodioxole (DMB) at a concentration of 1.25 ppm to 20 ppm.

2. The method according to claim 1, wherein the c-Met regulatory composition further comprises an effective amount of Antrodin A, and the concentration of Antrodin A is at least 8.75 ppm and less than 140 ppm.

3. The method according to claim 2, wherein the concentration ratio of DMB to Antrodin A is 1:2 to 1:10.

4. The method according to claim 2, wherein the concentration ratio of DMB to Antrodin A is 1:5 to 1:10.

5. The method according to claim 1, where the c-Met regulatory composition is administered to regulate polygenes related to hepatocyte cytotheis and regeneration.

6. The method according to claim 1, further comprising administration of an antiviral drug.

* * * * *